(12) United States Patent
Fatherazi et al.

(10) Patent No.: US 8,746,515 B2
(45) Date of Patent: Jun. 10, 2014

(54) CLOSURE FOR A CONTAINER

(75) Inventors: Shahmir Fatherazi, Aachen (DE);
Gerhard Greller, Goettingen (DE);
Oscar-Werner Reif, Hannover (DE);
Magali Barbaroux, La Destroussen (FR); Michael Bates, Gloucester (GB)

(73) Assignee: Sartorius Stedim Biotech GmbH (DE)

( * ) Notice: Subject to any disclaimer, the term of this patent is extended or adjusted under 35 U.S.C. 154(b) by 0 days.

(21) Appl. No.: 13/132,572

(22) PCT Filed: Nov. 17, 2009

(86) PCT No.: PCT/EP2009/008176
§ 371 (c)(1),
(2), (4) Date: Jun. 2, 2011

(87) PCT Pub. No.: WO2010/063372
PCT Pub. Date: Jun. 10, 2010

(65) Prior Publication Data
US 2011/0233210 A1    Sep. 29, 2011

(30) Foreign Application Priority Data
Dec. 5, 2008 (DE) .......................... 10 2008 060 773

(51) Int. Cl.
*B65D 47/24* (2006.01)
(52) U.S. Cl.
USPC ......... 222/525; 222/522; 222/523; 220/254.9
(58) Field of Classification Search
USPC ................. 220/254.9, 254.1, 345.4, 345.1; 222/521, 522, 525, 181.1; 215/363, 215/264, 267
See application file for complete search history.

(56) References Cited

U.S. PATENT DOCUMENTS

| | | | | |
|---|---|---|---|---|
| 3,262,613 A | * | 7/1966 | Miller | 222/522 |
| 4,408,700 A | * | 10/1983 | Fillmore et al. | 222/153.06 |
| 4,413,806 A | * | 11/1983 | Anderson | 251/340 |
| 4,508,234 A | * | 4/1985 | Bartholomew | 215/206 |
| 4,946,080 A | * | 8/1990 | Vesborg | 222/500 |
| 5,975,369 A | | 11/1999 | Yurkewicz et al. | |
| 6,065,651 A | * | 5/2000 | Tedeschi et al. | 222/519 |

(Continued)

FOREIGN PATENT DOCUMENTS

| | | | | |
|---|---|---|---|---|
| EP | 1 065 150 | | 1/2001 | |
| FR | 2674508 A1 | * | 10/1992 | ............. B65D 47/14 |
| FR | 2698078 A1 | * | 5/1994 | ............. B65D 47/28 |
| WO | 2005/044685 | | 5/2005 | |

OTHER PUBLICATIONS

International Preliminary Report of Patentability.

*Primary Examiner* — Fenn Mathew
*Assistant Examiner* — Chetan Chandra
(74) *Attorney, Agent, or Firm* — Gerald E. Hespos; Michael J. Porco; Matthew T. Hespos

(57) ABSTRACT

A closure for a container has an upper part (1) that can be connected to the container. The upper part (1) has an opening (2) and an outer hollow body (3). An inner hollow body (4) is arranged coaxially in the outer hollow body (3) with an intermediate space therebetween. A lower part (7) in the form of a hollow body can be displaced longitudinally in the intermediate space. A plug (5) is held coaxially in the lower part (7) and opens or closes the opening as the lower part (7) is displaced longitudinally in the intermediate space.

20 Claims, 5 Drawing Sheets

(56) References Cited

U.S. PATENT DOCUMENTS

| | | | | |
|---|---|---|---|---|
| 6,142,341 | A * | 11/2000 | Uematsu | 222/92 |
| 6,257,453 | B1 * | 7/2001 | Graham | 222/153.06 |
| 6,257,463 | B1 * | 7/2001 | De Polo | 222/525 |
| 6,321,924 | B1 | 11/2001 | Yurkewicz et al. | |
| 6,758,359 | B2 * | 7/2004 | Yurkewicz et al. | 215/251 |
| 6,883,683 | B1 | 4/2005 | Cunningham et al. | |
| 7,588,142 | B1 | 9/2009 | Bush | |
| 7,614,607 | B2 * | 11/2009 | Stiers | 251/340 |
| 7,806,303 | B1 * | 10/2010 | Hastings | 222/481.5 |
| 8,152,017 | B2 * | 4/2012 | Lizerbram et al. | 220/254.9 |
| 2003/0121879 | A1 | 7/2003 | Smith et al. | |
| 2004/0129741 | A1 * | 7/2004 | Stoneberg et al. | 222/521 |
| 2005/0121477 | A1 * | 6/2005 | Scott | 222/522 |
| 2007/0102450 | A1 * | 5/2007 | Stiers | 222/181.1 |
| 2008/0041891 | A1 * | 2/2008 | Bradley | 222/521 |

* cited by examiner

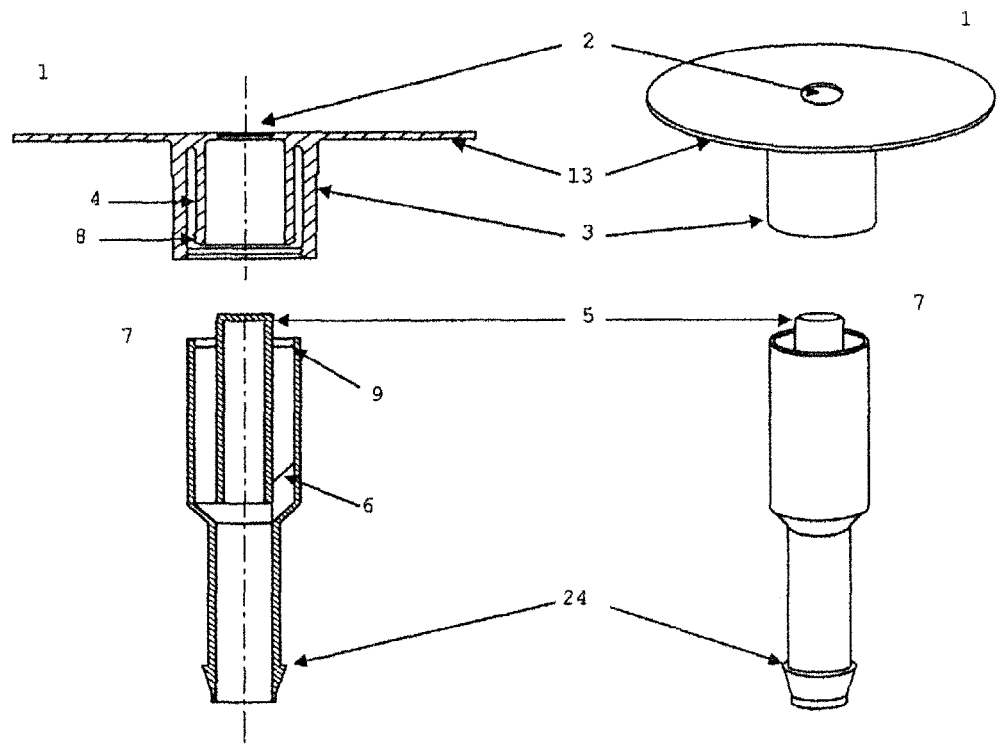
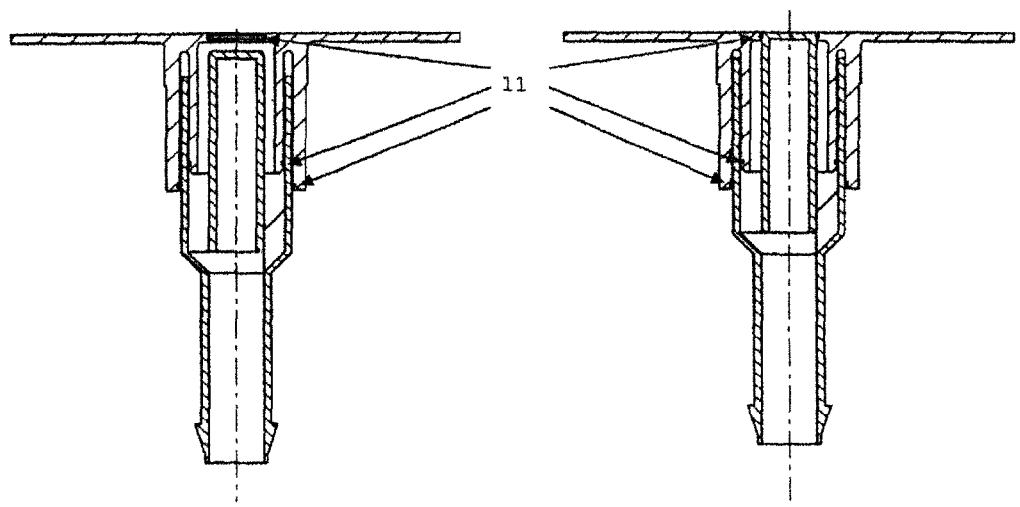
Figure 1a        Figure 1b
Figure 2a        Figure 2b

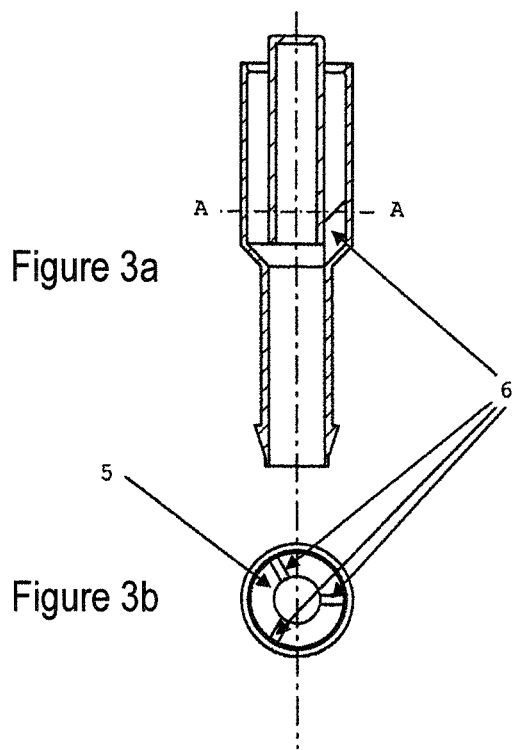
Figure 3a
Figure 3b
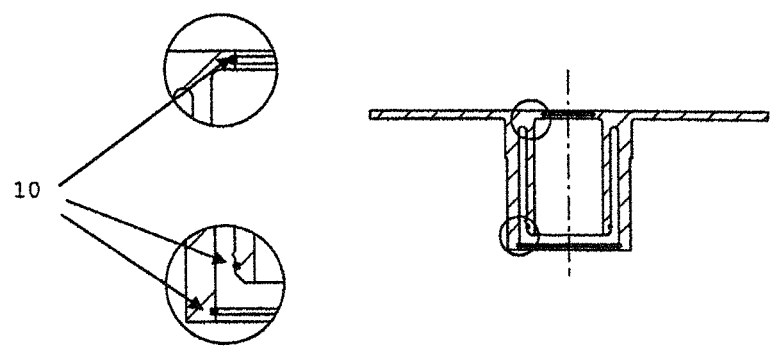
Figure 4

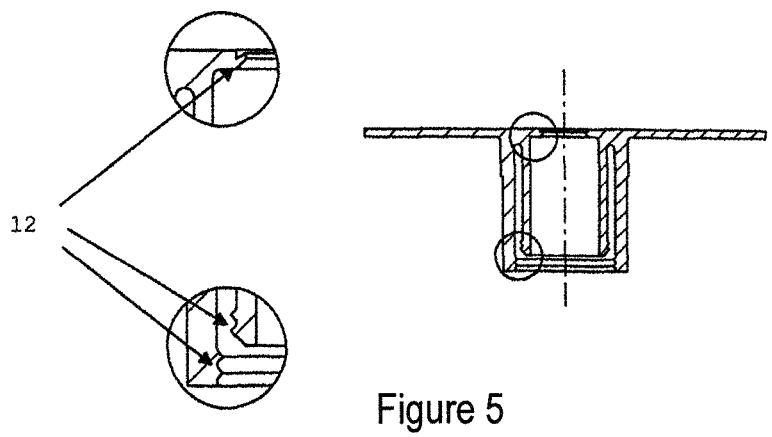
Figure 5
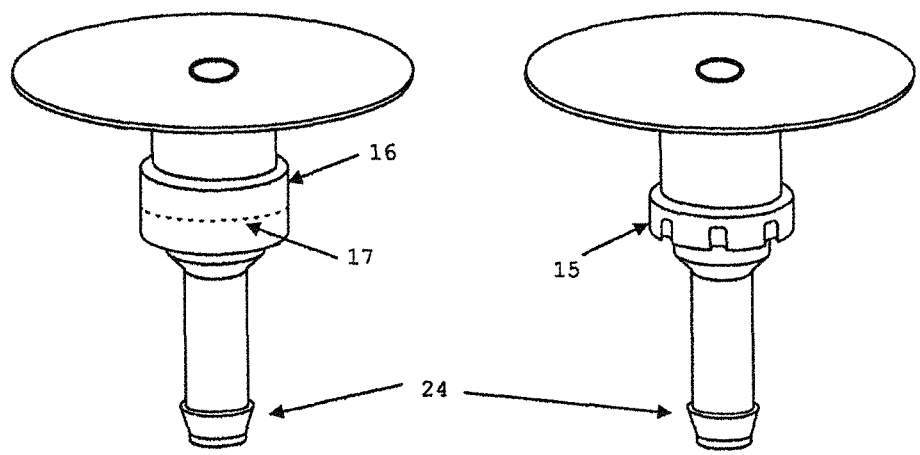
Figure 6                    Figure 7

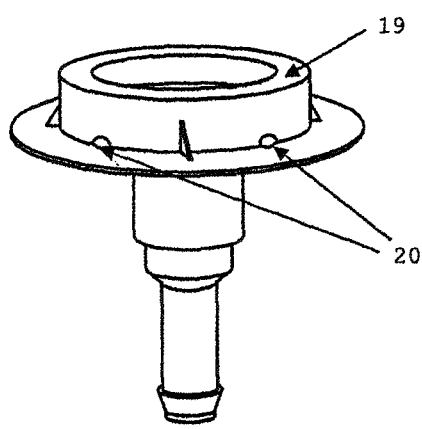
Figure 8
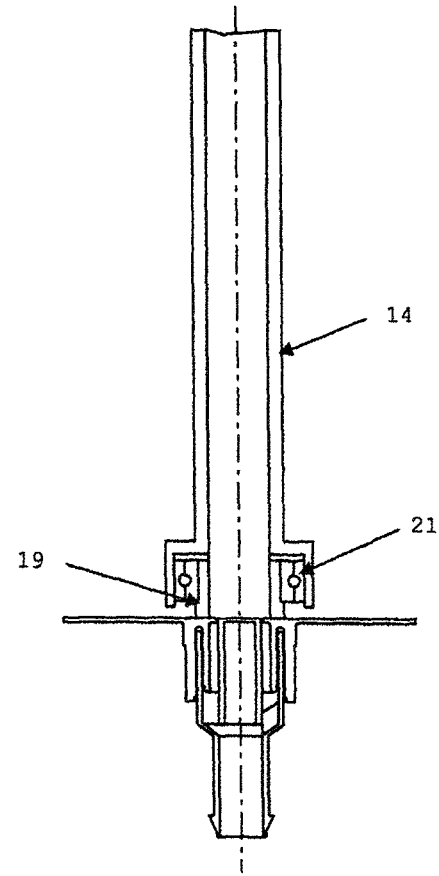
Figure 9
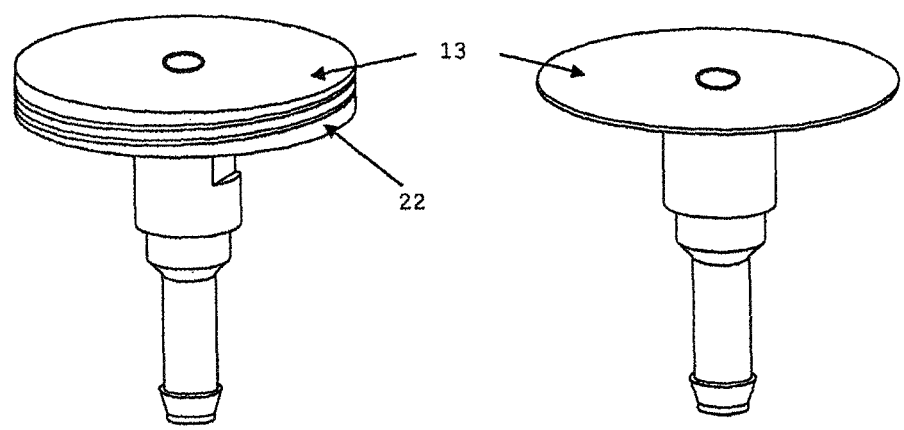
Figure 10
Figure 11

CLOSURE FOR A CONTAINER

BACKGROUND OF THE INVENTION

1. Field of the Invention

The invention relates to a closure for a container, said closure ensuring supply and removal of media. A closure of this type is used in particular for single-use reactors, mixing reactors and bioreactors in pharmaceutics and biotechnology.

2. Description of the Related Art

The closure of a container is known in many different embodiments. For containers in the sphere of laboratory technology and in industrial use, such as in the pharmaceutical production of products or in foodstuff technology, closures are required which can be handled simply and reliably. A particularly cost-effective production is required in particular in the sphere of single-use products.

U.S. Pat. No. 5,975,369 discloses a drinking bottle closure, in which a first sleeve which is connected to the drinking bottle has a cylindrical ram. The closure furthermore has a second cylindrical sleeve having a smaller diameter than the diameter of the first sleeve connected to the bottle, wherein the cylindrical sleeve having the smaller diameter has, at its upper end, an opening which, in the closed state of the bottle, is closed by the cylindrical ram. The cylindrical sleeve having the smaller diameter can be displaced axially along the ram. By means of locking devices on the ram and the sleeve having the smaller diameter (for example by means of stops on the inner wall of the sleeve having the smaller diameter), the sleeve having the smaller diameter is prevented from being pulled off from the ram. In this case, it has proven disadvantageous that there is a dead space in the closure itself. There are structurally induced clearances between the cylindrical sleeves and on the ram. Correct use for, for example, drinking bottles permits the medium to flow back into the container, since an attachment to the container cover is provided. When attached to the bottom of a container, a closure of this type would create space for a medium which remains in said clearance. A closure of this type is unfavorable for use on a single-use reactor, mixing or bioreactor, since the portion of medium remaining in the dead space of the closure is not subjected to the same conditions as the medium in the container. It is also possible for particles to be deposited in the dead space and to block the latter up.

US 2003/0121879 A1, U.S. Pat. Nos. 6,758,359 B2, 6,321,924 B1 and WO 2005/044685 A1 disclose bottle closures for beverage and cleaning agent containers, said bottle closure constituting further developments of the closure disclosed in U.S. Pat. No. 5,975,369 in respect of the configuration of the sleeves, the ram and a protective cap covering said components. Even the further developments do not solve the problem of the dead space, since the correct use is entirely different.

Finally, US 2007/0102450 A1 discloses a closure for a container, which has a closure part, a flange and two sealing rings, wherein the closure part is a hollow piston which is closed at one end and is open at the other end, and wherein there are bores below the closed side, through which the medium flows when the closure is open. Seals are located above and below the bores. In the closed state, the closed side together with the upper sealing ring closes the flange opening.

In a first embodiment disclosed in US 2007/0102450 A1, the hollow piston can be displaced into the container for the opening. A disadvantage in this case is that a part which projects into the container interferes with elements which can be provided on the inside of the container, such as, for example, stirrers or gas-injecting devices, which are preferably, like a closure, provided centrally.

In a second embodiment, the hollow piston can be pulled back out of the container into a "preliminary space". In the open state of the closure, the medium passes into the preliminary space and from there through the bores into the hollow piston. A disadvantage here is the absence, caused by the construction, of locking, and therefore there is no security against unintentionally completely pulling out the hollow piston. A further disadvantage is the unfavorable deflection of the container contents during the outlet operation. The medium is repeatedly deflected via the closed end and by means of the bores which are located in the preliminary space in the open state, and therefore experiences a relatively high degree of flow resistance. This firstly has a negative effect on substances which are sensitive to shearing and secondly the volumetric flow is therefore reduced, which leads to the container taking longer to empty. The preliminary space has furthermore proven disadvantageous when the closure is in a closed state. In the event of a leakage at the sealing ring attached to the container interior, but also in the case of inadequate or defective closing, the preliminary space would fill with the medium. In the case of small leakages, the preliminary space fills first of all and the medium passes only after some time through the bores into the hollow piston and from there into the outlet tube. Furthermore, the preliminary space results in a dead space which is not desirable with regard to a hygienic design. Possible cleaning therefore becomes problematic, and, for example, bacteria could multiply or cells could die. It is also possible for substances remaining behind to develop differently and, during removal of the medium which, by the closure being opened, inevitably comes into contact with substances remaining back in the preliminary space, corresponding analyses are falsified.

A joint disadvantage of both embodiments of US 2007/0102450 A1 is that, in the event of a leakage at both seals or, in the open state, if there is a leakage at the seal below the bores, the container contents emerge into the open. This may lead to a hazardous contamination of staff and/or the environment and furthermore jeopardizes a sterile state which is to be maintained.

The invention is therefore based on the object of providing a closure for a container, which closure does not have any dead space, and has favorable guiding of the media and a high degree of security.

SUMMARY OF THE INVENTION

The closure according to the invention for a container comprises an upper part and a lower part. The upper part can be connected to the container and has an opening. Furthermore, it has an outer hollow body and an inner hollow body which is arranged coaxially with the latter and, together with the outer hollow body, forms an intermediate space.

The opening is closed by a plug. The PLUG is held coaxially in a lower part, which is in the form of a hollow body, by means of at least one retaining device. In order to open the opening, the upper section of the lower part can be displaced longitudinally in the intermediate space away from the container, and the longitudinal displaceability of the lower part is restricted by locking devices. It is therefore ensured that, for the opening and closing, objects are not moved into the region on the inside of the container. While the handling is desirably simple, the locking devices at the same time prevent the lower part from being pulled off, and therefore take on an important securing function. Hectic, rapid or overvigorous opening is therefore absorbed. Furthermore, the closure essentially comprises the two parts, the upper part and lower part, which can each be manufactured simply and cost effectively and joined together. A further important advantage is the manner of guiding the media. A preliminary space, and therefore dead space, for the medium is dispensed with by the container having a rectilinear transition in the opening into a line via the closure. By means of the coaxial hollow bodies and the lower part, which is held and can be guided in a longitudinally displaceable manner therein and is in the form of a hollow body, the medium is guided into the container or out therefrom in a rectilinear, simple and protective manner. Furthermore, the construction means that the medium cannot pass to the outside, thus avoiding contamination of the environment and damage to individuals.

According to a preferred embodiment of the invention, the locking devices are arranged on the inner wall of the lower part and on the outer wall of the inner hollow body. This can be realized simply and cost-effectively by injection molding. The push and pull handling can therefore lead reliably and simply to opening and closing of the closure. At the same time, complete pulling off is effectively prevented. The design of the closure also permits flexible material to be able to used for the production thereof, since the geometrical arrangement in relation to one another of outer cylinder, inner cylinder and the lower part with a plug prevents bending, for example of the inner cylinder, by vigorous opening, and therefore prevents the locking devices from moving above one another.

In a particularly preferred embodiment of the closure according to the invention, in the closed state, the upper end of the plug ends flush with the upper part. There are therefore no protruding parts in the container that have an adverse effect on elements, such as stirrers, gas-injecting units, etc., being provided on the inside of the container. Like said elements, a closure preferably also is arranged as centrally as possible on the container bottom.

In a further preferred embodiment of the closure, the plug is sealed off from the opening of the upper part by a sealing ring, for example an O-ring. This ensures a secure and tight closure. One embodiment may be a sealing ring around the plug. A further embodiment comprises, for example, attaching the sealing ring to the opening.

In the case of these above-mentioned, preferred embodiments of the closure according to the invention, in the open state, the opening enables media to be removable from the container or suppliable to the container through the intermediate space between the inner wall of the inner hollow body and the plug. These above-mentioned embodiments permit media to be supplied, in particular in sterile form, to the container or to be removed therefrom in sterile form.

In a further advantageous refinement of the invention, the inner wall of the outer hollow body and the outer wall of the inner hollow body each have at least one sealing element. The medium can therefore flow in and out in sterile form, and there is no dead space for a medium which emerges or has already emerged through the opening due to a defective closure or because of leakage or which may accumulate in the closure after being let out or admitted. As a result, there is also a further, additional securing means which prevents leakage from emerging into the environment. Contamination of the environment is therefore avoided and a risk to individuals is ruled out. If a container is already full, the minimal flow resistance enables the medium to flow past the plug directly into the lower part and from there into a discharge line. The medium behaves in the same manner when flowing into the container. However, in the case of high volumetric flows, it is possible for parts of the media flow to pass along the outer wall of the inner hollow body into the region between the inner and outer hollow bodies. An escape is therefore effectively prevented by means of sealing elements at the above-mentioned region.

According to a further particularly preferred embodiment of the closure according to the invention, the outer hollow body and/or in the inner hollow body and/or the lower part are of rotationally symmetrical design. The shape is preferably round. The production and the handling are therefore made easier. In particular in the case of a cylindrical design, connectivity to tube lines or pipes is simplified.

In a further advantageous refinement of the invention, the outer hollow body and/or the inner hollow body and/or the lower part are of polygonal design.

According to a further preferred embodiment of the invention, the locking devices are encircling sealing lips or ribs. Locking devices of this type ensure an effective barrier against the lower part being pulled off from the upper part. For example, sealing lips can be used for guiding the upper part and lower part in one another in a simplified manner and for simultaneously locking the hollow body of the lower part within the inner and outer cylinders of the upper part. By means of a projection which is beveled on one side, sealing lips of this type permit simple plugging one inside the other and prevent a subsequent pulling out beyond said point.

In a further preferred embodiment of the invention, the at least one retaining device is a web which is attached to the inner wall of the lower part and retains the plug.

According to a further preferred embodiment of the invention, the lower region of the lower part is of conical design. In this case, the expression "lower region" is to be understood as meaning relative to the container when the closure is attached thereto. By means of the conical region, tube lines can be connected securely, fixedly and rapidly. Other embodiments of the lower region of the lower part, such as threads for pipes, clamping connections, etc., are also possible. The diameter can be varied as desired.

According to a further preferred embodiment of the invention, the closure can be connected to the container, for example by being screwed in, adhesively bonded in, clamped in or welded in. The upper region of the upper part is preferably designed as a disk which is pierced by the opening and can be connected to the container by above-mentioned connecting options.

According to a further particularly preferred embodiment of the invention, the container is a reactor for single use and is formed from flexible plastic. In particular in the case of single-use products, it is necessary to provide closures which are cost-effective, but are nevertheless secure and simple to handle, which is achieved by the invention.

According to a further preferred embodiment of the closure according to the invention, a stem of a mixing device of the container, or a gas-injecting device, can be held by the upper part. By means of the embodiment according to the invention as a closure which does not project into the container interior, it is possible, for example, for a stirrer or a gas-injecting device to be provided centrally, like the closure itself, since stirrers or gas-injecting devices require a uniform distribution of the part of the process which they produce (flow, gas bubbles). A stirrer is likewise preferably attached on both sides, since this enables a particularly high degree of stability to be achieved. A holding device can be, for example, attached to the closure or integrated therein.

According to a further preferred embodiment of the invention, the closure is additionally secured against an unintentional opening by means of a union nut, a bayonet closure, a torsional snap-in connection or a sleeve with a predetermined breaking point. Said devices can furthermore fulfill an indicator function, for example in conjunction with RFID devices or computer program products which register and store the unintentional opening of the closure and provide the information to a user in readable form. A further example is a sleeve with predetermined breaking points. The sleeve is connected on one side via collars to the upper part and on the other side to the lower part and keeps said parts one inside the other. By rotation of the collars counter to one another or of the lower part in relation to the upper part, the sleeve breaks at predetermined breaking points and the closure can be opened. A breakage at the sleeve can then be used as an indicator which indicates the use of the outlet and therefore leads to greater process security and control.

According to a further preferred embodiment of the invention, the upper part and the lower part each have a screw thread, and the lower part can be screwed into the upper part. For example, even small quantities of the medium can therefore be let out in a controlled manner.

FIGS. 1a to 13 show different embodiments of the closure for a container.

BRIEF DESCRIPTION OF THE DRAWINGS

FIG. 1a shows a cross section through an exemplary embodiment.

FIG. 1b shows a perspective view of an exemplary embodiment.

FIG. 2a shows a sectional view through an exemplary embodiment of the closure for a container in the open state.

FIG. 2b shows a sectional view through an exemplary embodiment of the closure for a container in the closed state.

FIG. 3a shows a sectional view through an exemplary embodiment of the lower part.

FIG. 3b shows a top view of an embodiment of the lower part along the section line A-A of FIG. 3a.

FIG. 4 shows a detailed view of an embodiment of the upper part with sealing rings.

FIG. 5 shows a detailed view of an embodiment of the upper part with sealing lips.

FIG. 6 shows a perspective view of an exemplary embodiment of the closure for a container with a sleeve having a predetermined breaking point.

FIG. 7 shows a perspective view of an exemplary embodiment of the closure for a container with securing by means of a union nut.

FIG. 8 shows a perspective view of an exemplary embodiment of the closure for a container with a receptacle for the mounting of a stirrer rod including through bores.

FIG. 9 shows a cross section through a closure for a container according to FIG. 8 with a receptacle for the mounting of a stirrer rod including stirrer rod and bearings.

FIG. 10 shows a perspective view of an exemplary embodiment of the closure for a container in the form of a screwing-in version.

FIG. 11 shows a perspective view of an exemplary embodiment of the closure for a container in the form of a welding-on version.

DETAILED DESCRIPTION OF THE PREFERRED EMBODIMENTS

Figure 12:
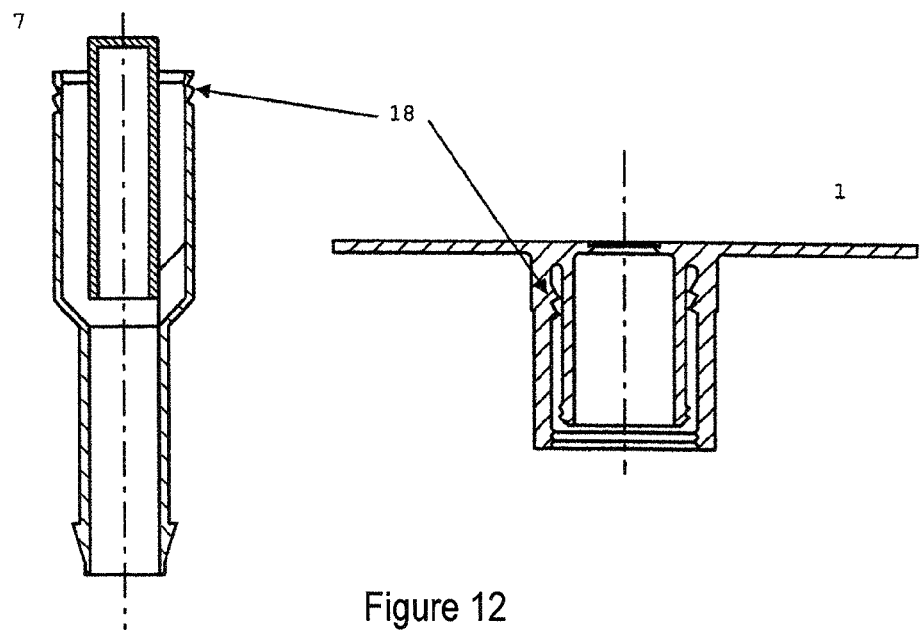
FIG. 12 shows a cross section through an exemplary embodiment of a closure for a container with a screw thread.

According to FIG. 1a to FIG. 2b, the closure for a container comprises an upper part 1, which can be connected to the container, and a lower part 7. The upper part has an opening 2 and has an outer hollow body 3 and an inner hollow body 4 arranged coaxially with the latter. The inner hollow body 3 and the outer hollow body 4 form an intermediate space with each other. In order to close the opening 2, a plug 5 is held coaxially in the lower part 7, which is in the form of a hollow body, by means of at least one retaining device 6, whereas, in order to open the opening 2, the upper region of the lower part 7 can be displaced longitudinally in the intermediate space away from the container. The longitudinal displaceability of the lower part 7 is restricted by locking devices 8, 9.

FIG. 1a shows a cross section through an exemplary embodiment of the closure for a container, wherein the upper part 1 and the lower part 7 are illustrated separately from each other. The same exemplary embodiment is illustrated perspectively in FIG. 1b and as a cross section in the open state in FIG. 2a and in the closed state in FIG. 2b. Possible sealing elements 11 are indicated therein.

FIG. 3b shows a top view of the lower part 7 along the section line A-A of FIG. 3a. In this exemplary embodiment, three plug retainers 6 have been provided for the fastening of the plug 5. Along with sufficient space for the flowing medium, this results in a satisfactory degree of stability for the plug 5. A different arrangement, type and number of retaining devices 6 are likewise possible.

FIG. 4 and FIG. 5 are detailed views of respective exemplary embodiments with sealing rings 10 (FIG. 4) and sealing lips 12 (FIG. 5).

FIG. 6 and FIG. 7 perspectively show embodiments of the closure for a container with securing by means of a union nut 15 (FIG. 7) or by means of a sleeve with one or more predetermined breaking points 17 (FIG. 6). The sleeve 16, as illustrated in FIG. 6, is fastened, for example, by the upper region to the upper part 1 and by the lower region to the lower part 7. Said fastening can take place, for example, via collars. The presence of one or more predetermined breaking points 17 makes it easier to open the closure and can serve at the same time as an indicator. Prior use and inadvertent opening can therefore be recognized and the sterility can be maintained. In addition, a sleeve 16 securely and effectively keeps the upper part 1 and the lower part 7 together. Said keeping of the upper and lower parts 1 and 7 together can also be ensured with the aid of a union nut 15, as illustrated in FIG. 7. At the same time, such an embodiment can also serve as an opening and closing mechanism when, for example, the union nut 15 is fixedly connected at its lower region to the lower part 7 and, via its internal or external thread, depending on the embodiment, can be screwed or unscrewed around the corresponding mating thread on the upper part. A likewise rotatably mounted tube connection 24 or a similar type of device can additionally counteract rotation of the line 25.

The exemplary embodiment of FIG. 8 perspectively shows a closure for a container with a receptacle, which can be connected to the upper part 1, for the mounting of a stem 14 including through bores 20. For example, any apparatus parts used in bioreactors, such as, for example, a gas-injecting device or a stirrer, are conceivable for the mounting receptacle 19. In order to continue to ensure a passage for the medium between the container interior and closure, through bores 20, for example, on the mounting receptacle 19 or other apertures are possible. The mounting receptacle 19 can be produced as a permanent part of the upper part 1, for example integrally by means of injection molding, or can be attached afterwards as a separate device to the upper part 1, for example by adhesive bonding, welding, or clamping or screwing in. It is also possible to connect the mounting receptacle 19 directly to the container. An exemplary embodiment with a stem 14 illustrated sitting in the mounting receptacle 19 is illustrated in cross section in FIG. 9. A bearing 21 which sits on the mounting receptacle 19 and rotatably supports a stirrer stem is illustrated here. The stem 14, as already mentioned, may also constitute part of a different apparatus or may serve to stabilize the container.

FIG. 10 and FIG. 11 represent further exemplary embodiments of the upper part 1 of a closure for a container. The closure can be manufactured from any materials in accordance with requirements, needs or for material consistency reasons. For example, the disk 13 can be designed as a screw-in part and can be equipped with a thread 22, as is frequently provided for metal containers, as illustrated in the perspective view of FIG. 10. An embodiment of this type made of plastic or other materials is also conceivable. FIG. 11 perspectively shows an exemplary embodiment which, as a welding-on part or adhesive bonding part, permits welding or adhesive bonding onto an inner or outer wall of the container. In the event of using plastic containers, for example, the upper part 1 preferably has a disk 13 which is welded to the wall of the plastic container.

The embodiment illustrated in cross section in FIG. 12 has a screw thread 18 for the closure. The upper part 1 and the lower part 7 are each provided with a thread such that the lower part 7 can be screwed into the upper part 1. The closure is opened or closed by rotation of the lower part 7 counter to the upper part 1. For this purpose, as illustrated in FIG. 12, the lower part 7 on the outer wall of the outer hollow body 3 can be provided with an internal thread, and the upper part 1 on the inner wall of the outer hollow body 3 can be provided with an external thread. The screw threads 18 may also be provided or integrated at different locations and also interchanged as desired in their type of embodiment (internal or external threads), for example by an external thread being provided or integrated on the inner wall of the lower part 7, and an internal thread being provided or integrated on the outer wall of the inner hollow body 4. It is also possible to provide a female thread by boring between the outer hollow body 3 and the inner hollow body 4, into which female thread the lower part 7, embodied as a male thread, can be screwed. The screw thread 18 may be designed, for example, as a metric ISO thread, Whitworth thread, pipe thread, trapezoidal thread, round thread or buttress thread. The use of a screw thread 18 enables a medium to be supplied and removed in a controlled manner. If, for example, a fine screw thread is used, the slight advance per rotation permits precise adjustments. The embodiment with a thread generally provides a high degree of stability, strength, flexibility and security.

Figure 13:
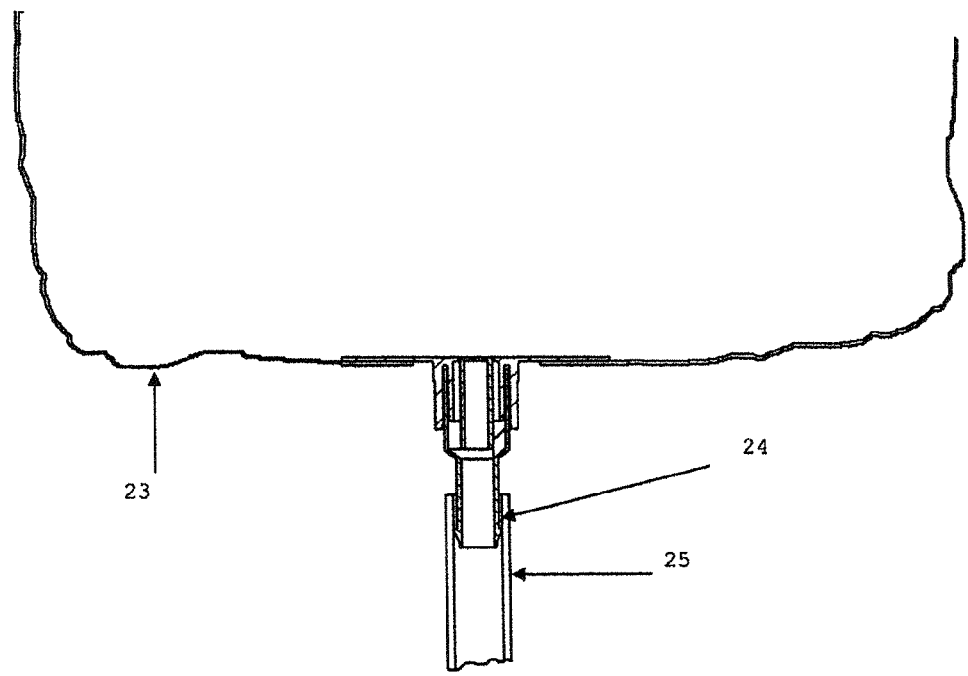
FIG. 13 shows a cross section through an exemplary embodiment of a closure on a container with a line attached to the tube connection.

FIG. 13 shows a cross section through an exemplary embodiment of the closure for a container, wherein the upper part 1 is illustrated fastened to a single-use container 23. For reasons of clarity, only one region of the single-use container 23 is illustrated without additional elements. The lower part 7, for its part, is joined together with the upper part 1 and is illustrated with a line 25 which is attached to the tube connection 24 of the lower part 7. The lower part 7 can generally be adapted to any tube or pipe diameter.

The invention claimed is:

1. A closure for a container, comprising:
   an upper part (1) having a disc (13) that can be connected to the container, the upper part (1) having an opening (2) for communicating with an interior of the container when the disc (13) is connected to the container, an outer hollow body (3) projecting from the disc (13) in a direction away from the container and an inner hollow body (4) arranged coaxially within the outer hollow body (3) and outward of the opening (2) with an intermediate space defined between the inner and outer hollow bodies (4, 3), the inner hollow body (4) projecting from the disc (13) by a selected length,
   a lower part (7) having an upper region and a tubular lower region, the upper region having an outer tube that extends from an upper end of the tubular lower region and that is longitudinally displaceable in the intermediate space for movement toward and away from the container with the outer hollow body (3) of the upper part (1) being telescoped over the outer tube, locking devices (8, 9) configured for restricting longitudinal displaceability of the lower part (7) in the intermediate space, a plug (5) held coaxially in the outer tube of the lower part (7) by circumferentially spaced retaining devices (6) axially beyond the inner hollow body (4), the outer tube and the plug (5) projecting from the retaining devices (6) sufficient distances relative to the selected length of the inner hollow body (4) to enable the plug (5) to close the opening (2) when the lower part (7) is moved relative to the upper part (1) toward the container (23) and to open the opening (2) and to permit fluid communication from the container (23) to the tubular lower region when the lower part (7) is moved relative to the upper part (1) away from the container (23).

2. The closure of claim 1, wherein the locking devices (8, 9) are arranged on an inner wall of the lower part (7) and on an outer wall of the inner hollow body (4).

3. The closure of claim 1, wherein, an end of the plug (5) ends flush with the upper part (1) when the plug (5) is disposed for closing the opening (2).

4. The closure of claim 1, wherein the plug (5) is sealed off from the opening (2) of the upper part (1) by a sealing ring (10) or sealing lips (12).

5. The closure of claim 1, wherein the opening (2) is disposed and configured to enable media to be removed from the container or supplied to the container through an annular space between the inner wall of the inner hollow body (4) and the plug (5) when the plug (5) is disposed for opening the opening (2).

6. The closure of claim 5, wherein the media can be removed or supplied in sterile form.

7. The closure of claim 1, wherein an inner surface of the outer hollow body (3) and an outer surface of the inner hollow body (4) each have at least one sealing element (11).

8. The closure of claim 1, wherein the outer hollow body (3), the inner hollow body (4) and the lower part (7) each have a round cross section.

9. The closure of claim 1, wherein the outer hollow body (3), the inner hollow body (4) and the lower part (7) each have a polygonal cross section.

10. The closure claim 1, wherein the locking devices (8, 9) are encircling sealing lips (12) or ribs.

11. The closure of claim 1, wherein the retaining devices (6) are webs attached to an inner surface of the lower part (7) and to the plug (5).

12. The closure of claim 1, wherein the lower region of the lower part (7) is conical.

13. The closure of claim 1, wherein the closure can be connected to the container by being screwed in, adhesively bonded, clamped or welded.

14. The closure of claim 1, wherein the container is a reactor for single use.

15. The closure of claim 1, wherein the reactor is formed from flexible plastic.

16. The closure of claim 1, wherein the upper part (1) is configured to hold a stem (14) of a mixing device of the container.

17. The closure of claim 1, wherein the upper part (1) is configured to hold a gas-injecting device.

18. The closure of claim 1, wherein the closure is secured against an unintentional opening by a union nut (15), a bayonet closure, a torsional snap-in connection or a sleeve (16) with one or more predetermined breaking points (17).

19. The closure of claim 1, wherein the upper part (1) and the lower part (7) each have a screw thread (18), and the lower part (7) can be screwed into the upper part (1).

20. The closure of claim 1, wherein the plug (5) has a projecting end that projects beyond the upper region of the lower part (7).

* * * * *